United States Patent
Kaneko et al.

(10) Patent No.: US 7,212,929 B2
(45) Date of Patent: May 1, 2007

(54) MOISTURE DATA-ACQUIRING DEVICE AND IMAGE-FORMING APPARATUS

(75) Inventors: Norio Kaneko, Atsugi (JP); Takehiko Kawasaki, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/144,647

(22) Filed: Jun. 6, 2005

(65) Prior Publication Data

US 2005/0271403 A1    Dec. 8, 2005

(30) Foreign Application Priority Data

Jun. 7, 2004  (JP) .............................. 2004-169114
May 18, 2005 (JP) .............................. 2005-146036

(51) Int. Cl.
*G01N 3/32* (2006.01)

(52) U.S. Cl. ....................................................... 702/50
(58) Field of Classification Search ................... 702/50
See application file for complete search history.

(56) References Cited

U.S. PATENT DOCUMENTS

2006/0016996 A1*  1/2006  Kaneko et al. .......... 250/339.1
2006/0022400 A1*  2/2006  Kawasaki et al. .......... 271/227

FOREIGN PATENT DOCUMENTS

| JP | 5-118984 | 5/1993 |
|---|---|---|
| JP | 5-164690 | 6/1993 |
| JP | 2000-156834 | 6/2000 |

* cited by examiner

*Primary Examiner*—Michael Nghiem
*Assistant Examiner*—Cindy D. Khuu
(74) *Attorney, Agent, or Firm*—Fitzpatrick, Cella, Harper & Scinto

(57) ABSTRACT

A moisture data-acquiring device has a force-applying unit for applying an external force to a sheet, a force-receiving unit for receiving the external force through the sheet, a signal outputting unit for outputting a signal reflecting a mechanical property of the sheet which unit is placed on at least one of the force-applying unit and the force-receiving unit, and a moisture data-acquiring unit for acquiring data on moisture of the sheet based on the signal from the signal outputting unit.

7 Claims, 7 Drawing Sheets

MOISTURE DATA-ACQUIRING DEVICE AND IMAGE-FORMING APPARATUS

BACKGROUND OF THE INVENTION

1. Field of the Invention

The present invention relates to a moisture data-acquiring device (a water content information-acquiring apparatus), and an image-forming apparatus.

2. Description of Related Art

Moisture-measuring devices are known as apparatuses for acquiring information on moisture such as a water content in a sheet material like recording paper sheets and postcards.

An example of the moisture-measuring device is an optical apparatus which determines the moisture content in a sheet material by measuring light absorption or light reflection.

The optical type device isolates light of the absorption wavelength 1.94 μm of water, and light of plural reference wavelengths from continuous spectrum light, for example, by a spectroscope or a wave filter, and measures the water content by comparison of absorbance or reflectivity of the light by water with those of the reference light (e.g., Japanese Patent Application Laid-Open Nos. H05-164690, and H05-118984).

Otherwise, a technique using a monochromatic light is disclosed to avoid use of a spectroscope or a wave filter not to enlarge the apparatus (e.g., Japanese Patent Application Laid-Open No. 2000-156834).

SUMMARY OF THE INVENTION

The above conventional optical type of moisture-measuring device requires essentially optical parts such as a light source, a light detector, and a spectroscope or filter. Further, the optical type of moisture-measuring device can be affected by dust from the sheet material or the like to cause variation of sensitivity of the photodetector. Therefore, a new type of moisture data-acquiring device is wanted.

The present invention intends to provide a device for acquiring information on the moisture in a sheet material, different from the aforementioned optical type apparatus.

According to an aspect of the present invention, there is provided a moisture data-acquiring device for acquiring data on moisture contained in a sheet, comprising:

a force-applying unit for applying an external force to the sheet;

a force-receiving unit for receiving the external force through the sheet;

a signal outputting unit for outputting a signal reflecting a mechanical property of the sheet which unit is placed on at least one of the force-applying unit and the force-receiving unit; and a moisture data-acquiring unit for acquiring data on moisture of the sheet based on the signal from the signal outputting unit.

The force-applying unit preferably applies the external force plural times to the sheet.

In the moisture data-acquiring device, a position-defining means is preferably provided for defining the position of the sheet to keep a constant distance between the force-receiving unit and the sheet.

The moisture data-acquiring unit preferably acquires the data on moisture of the sheet by the comparison of the signal from the signal outputting unit with data memorized in a memory on the relation between data on moisture of the sheet and signals from the signal outputting unit.

The force-applying unit preferably applies an external force to the sheet to bend and bring the sheet into contact with the force-receiving unit, and the contact causes output of the signal from the signal outputting unit. The sheet is preferably bent from the position of the sheet before the contact with the force-receiving unit by a concave or a groove provided on a side of the sheet on which the force-receiving unit is located.

According to another aspect of the present invention, there is provided an image-forming apparatus, comprising the above moisture data-acquiring device and an image forming assembly for forming an image on a sheet, wherein a condition for image formation is adjusted based on the data from the moisture data-acquiring device.

An image-forming apparatus, comprising the moisture data-acquiring device set forth in claim 1, an image forming assembly for forming an image on a sheet and a delivery means for delivering the sheet, wherein a condition for delivering sheet are adjusted based on data from the moisture data-acquiring device.

As described above, a novel type of moisture data-acquiring device can be provided according to the present invention.

DETAILED DESCRIPTION OF THE INVENTION

An embodiment of the present invention is explained by reference to FIG. 1.

Figure 1:
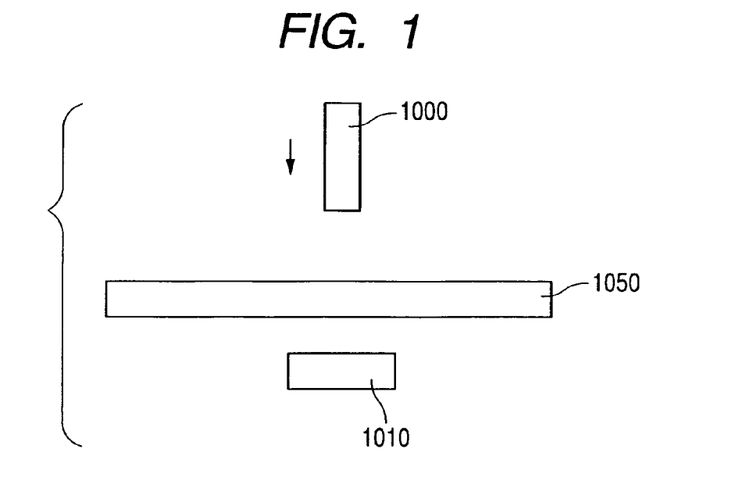
FIG. 1 is a schematic drawing for explaining the present invention.

In FIG. 1, force-applying unit 1000 applies an external force to sheet 1050. Force-receiving unit 1010 receives the external force through sheet 1050. A signal-outputting unit (not shown in the drawing) which outputs a signal reflecting the mechanical property of the sheet is provided on the side of the force-applying unit or on the side of the force-receiving unit.

The information on moisture contained in the sheet is acquired from the signal output from the signal-outputting unit by comparing the outputted signal with a preliminarily memorized data in the memorizing unit regarding the dependence of the outputted signal on the water content in the sheet material.

The data (or information) on moisture contained in the sheet includes a water content (%), an absolute quantity of water (g), a change of the water content corresponding to a change of the environment or handling history of the sheet material, and distribution of the water in the sheet face direction and the sheet thickness direction. In the present invention, the water content (%), for a sheet weight A (g) and a water quantity B (g) in the sheet, signifies the value of $[B/(A+B)]\times 100$ (%). The absolute quantity of water signifies a weight (g) of water contained in a sheet of any size. In the description below, the term "moisture" signifies the aforementioned information on water.

The principle of the present invention is described below briefly.

An external force applied to a sheet material will decay under action of the material of the sheet. The degree of the decay depends on the mechanical properties including compression strength and rigidity such as bending strength of the material of the sheet. The sheet will change its mechanical properties depending on the moisture quantity contained in the sheet.

Therefore, the data on moisture can be acquired from the aforementioned outputted signal by comparison with a preliminarily prepared chart or diagram memorizing the dependency of the outputted signal on the moisture quantity or a relative equation formula therefor.

For obtaining the moisture data, the external force may be applied one time, or several times at a constant strength or several times with the strength varied.

In one preferred embodiment, the external force applied by the force-applying unit bends the sheet to bring the sheet into contact with the force-receiving unit, whereby a signal is outputted from the signal-outputting unit. This embodiment is preferred since the signal reflects not only the compression strength but also degree of the bending of the sheet material. Incidentally, for bending of the sheet material by the applied force, a concave or a groove is provided on the impact-receiving side, which will be described later specifically.

In another preferred embodiment, the moisture data-acquiring device is mounted on an image-forming apparatus, and the moisture data is utilized for setting the conditions for image formation on the sheet in the image forming assembly (the conditions including an ink ejection quantity from an inkjet system, a toner fixation temperature in an electrophotograph system, etc.), or conditions for delivering the sheet material by a sheet delivering means (the conditions including a sheet delivery speed, a pressure between pinching rollers for delivery of the sheet, etc.).

The aforementioned moisture data-acquiring device can be used practically for a water content measurement.

The present invention is explained below more specifically by reference to drawings.

Figure 2:
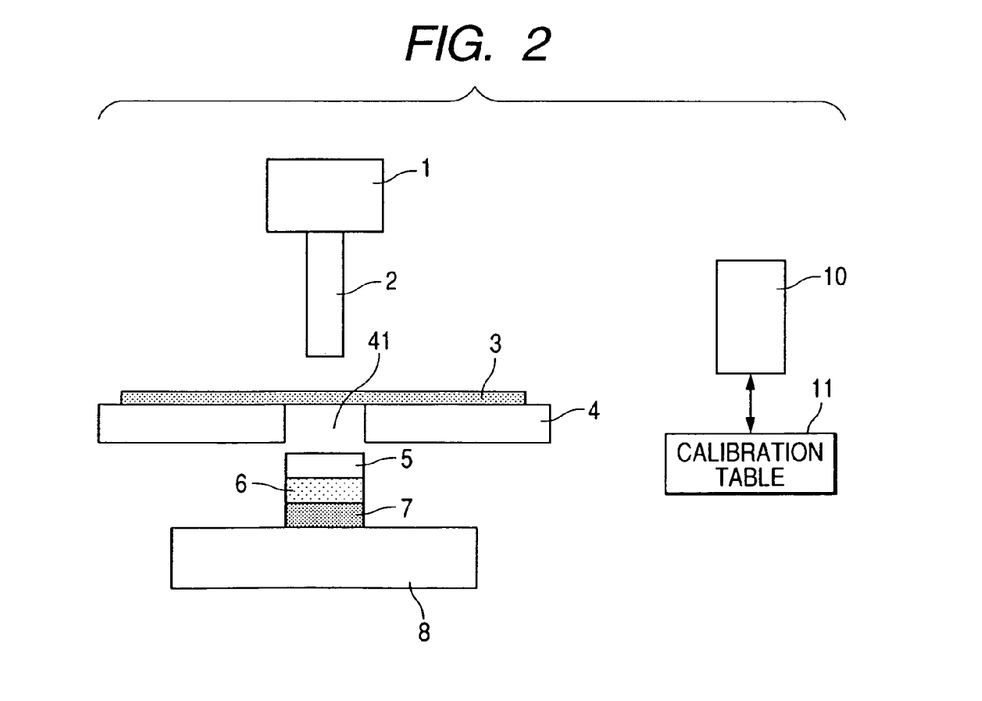
FIG. 2 is a schematic drawing for explaining an embodiment of the present invention.

FIG. 2 illustrates schematically constitution of a moisture-measuring device of a first embodiment of the present invention. In FIG. 2, force-applying unit 1 constituted of an external force-controlling means is controlled manually, automatically, or by a personal computer not shown in the drawing to produce a prescribed dynamic force and to controls the dynamic force. Force applying member 2 is driven by the force produced by force applying unit 1 toward sheet 3, downward in this embodiment.

Force-applying member 2 driven downward by the external force produced by force-applying unit 1 comes to collide against sheet 3 placed below. In this embodiment, force-applying unit 1 utilizes a motor, a cam, and a spring (not shown in the drawing) to allow force-applying member 2 to collide against sheet 3 to apply the external force thereto in every rotation of the motor.

Measurement table 4 as a sheet holding means holds sample sheet 3 at a measurement position. Measurement table 4 has rectangular aperture 41 at the position confronting the force-applying member 2. This aperture 41 may be circular or ellipsoidal, the shape being not limited. Force-applying member 2, when dropped, passed through-aperture 41 to collide against force-receiving member 5 confronting aperture 41.

This movement of force-applying member 2 bends sheet 3 downward through aperture 41 to collide against force-receiving member 5.

Pressure sensor 6 is placed in contact with the bottom face of force-receiving member 5. On collision of sheet 3 against force-receiving member 5 by action of force-applying member 2, the impact force of the collision is transmitted through force-receiving member 5 to pressure sensor 6. The pressure sensor 6 outputs an electric signal in correspondence with the transmitted impact force.

Moisture-measuring unit 10 receives the electric signal from pressure sensor 6, and detects the moisture in sheet 3 according to the electric signal from pressure sensor 6.

The rigidity of sheet 3 depends on the moisture content. Therefore at a fixed external force, the impact force transmitted by bending or compression of sheet 3 depends on the moisture content of sheet 3. Accordingly, the moisture content can be measured, by moisture-measuring unit 10, from the electric signal inputted from pressure sensor 6 as an external force-detecting means for detecting the impact strength transmitted through force-receiving member 5 based on the impact force strength.

In this embodiment, moisture-measuring unit 10 measures the moisture content in sheet 3 by comparing electric signal from pressure sensor 6 with calibration table 11 prepared preliminarily for the dependency of the electric signal on the moisture content in sheet 3.

In FIG. 2, force-receiving member 5, pressure sensor 6, and damping member 7 are bonded together by an adhesive to have a common center line with force-applying member 2, and aperture 41 of measurement table 4.

Pedestal 8 supports force-receiving member 5, pressure sensor 6, and damping member 7. Damping member 7, although not essential, is preferably provided to remove unnecessary vibration especially when pressure sensor 6 may generate noise by the vibration. In FIG. 2, the lead wiring is not shown.

In this embodiment, the periphery of aperture 41 serves as the fulcrum for bending the sheet 3. Therefore, the size of the aperture is preferably made changeable to meet the measurement purpose. Further, the level difference between the face of measurement table 4 for supporting sheet material 3 and the face of force-receiving member 5 is preferably made changeable to meet the purpose of the measurement. In other words, on application of an external force to the sheet, the bending extent and compression extent depend on the size of aperture 41 and the level difference between the face of measurement table 4 and the face of force-receiving member 5. Therefore, the aperture size is preferably selected to meet sheet 3 to be measured.

The aforementioned level difference is not limited. However, when the face of force-receiving member 5 is at the same level as or is higher than the face of measurement table 4, the compression extent of sheet 3 is defined. When the face of force-receiving member 5 is lower than the face of measurement table 4, the bending extent and compression extent of sheet 3 are defined. Therefore, when strong external force is applied, the level difference is adjusted not to cause breakage of sheet 3 or not to cause an irreversible change of the physical property thereof. In other words, measurement table 4 and force-receiving member 5 are placed in a relative position to define the deformation of sheet material 3 by the external force.

Figure 3:
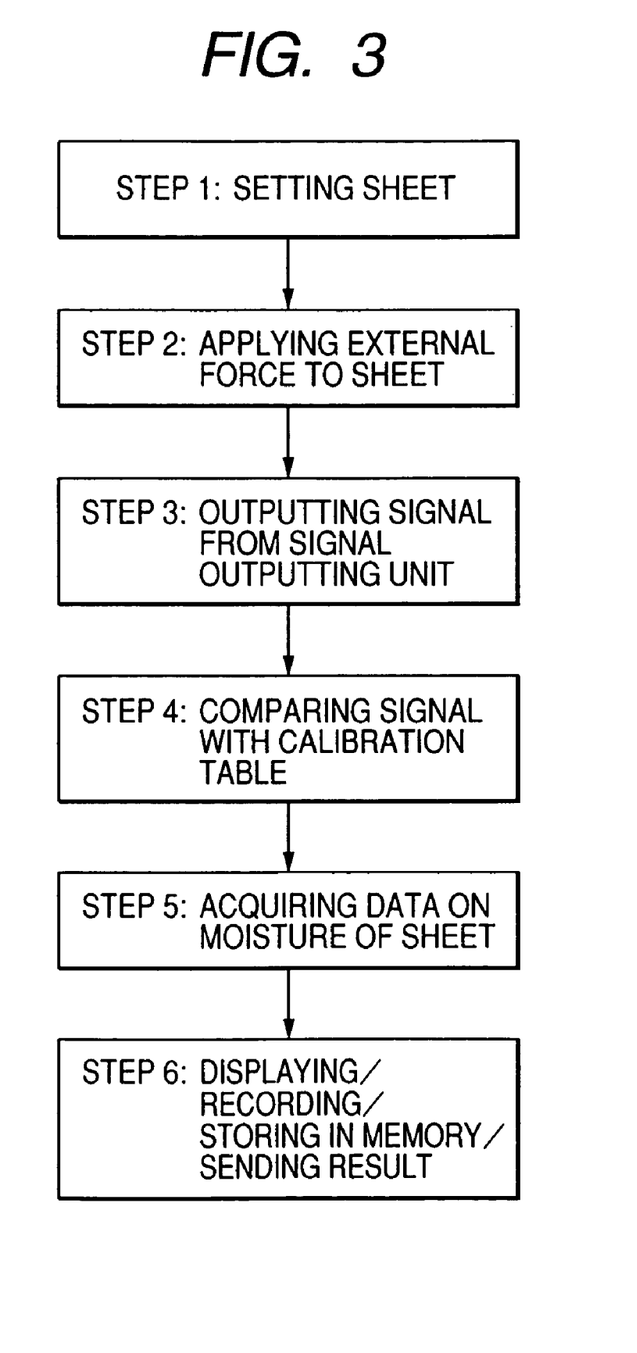
FIG. 3 shows steps of operation with the device of the present invention.

Next, the moisture measurement steps with a moisture-measuring device of the present invention are explained by reference to FIG. 3.

Firstly, sample sheet 3 is placed on measurement table 4 (Step 1). Then, an external force is applied by force-applying unit 1 through force-applying member 2 to sheet 3 (Step 2). For the external force application, the strength, application time, frequency, and so forth of the force are set by force-applying unit 1. This condition setting may be made automatically by an external means such as a personal computer not shown in the drawing.

On application of the external force, sheet 3 is bent to enter aperture 41 of measurement table 4 together with force-applying member 2 and collides against force-receiving member 5. The impact is transmitted to pressure sensor 6. That is, the applied force is transmitted through sheet material 3 (and force-receiving member 5) to pressure sensor 6.

Pressure sensor 6, on receiving the applied external force as an impact force through force-receiving member 5, outputs a detection signal reflecting the mechanical properties of sheet material 3 (Step 3). Pressure sensor 6 constituted of a piezoelectric element, for example, produces an electric signal.

The electric signal generated in the piezoelectric element is inputted to moisture-measuring unit 10, where the electric signal is compared with a preliminarily prepared calibration table 11 showing the dependence of the electric signal on the moisture content in sheet material 3 (Step 4). The moisture content in sheet material 3 is calculated (detected) by comparison of the electric signal with the calibration table (Step 5).

The result of the calculation (detection) is displayed, recorded, stored in a memory, or sent through the internet to complete the measurement (Step 6).

Figure 4:
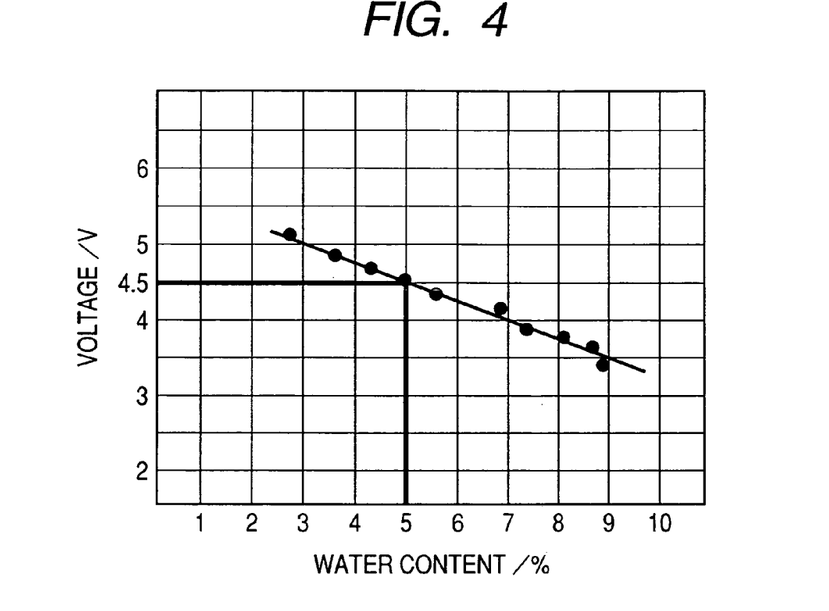
FIG. 4 shows results of measurement with the above device.

FIG. 4 shows a calibration table for electrophotographic paper sheets, FB75 (Fox River Bond Co.), as an example of sheet material 3. The calibration table shows the results of moisture measurement by a moisture-measuring device of the present invention with the paper sheets conditioned for 48 hours in a closed vessel kept at the measurement temperature of 25° C. and at controlled humidity.

In the above measurement, force-applying member 2 was a stainless steel round-column of 3 mm in diameter and 4 g in weight. Naturally the tip of the member may be rounded. Force applying unit 1 was set to allow force-applying member 2 to collide against the paper sheet at a velocity of 0.48 m/s by utilizing a motor, a cam, and a spring which are not shown in the drawing. The level difference between the face of measurement table 4 and the face of force-receiving member 5 was adjusted to 0.2 mm. Pressure sensor 6 employed was a piezoelectric element. The moisture content was measured with a paper moisture tester, Moistrex MX-5000E T80 (Shinmei General Co.). In the description below, this paper moisture tester is simply referred to a "paper moisture tester".

The output voltage from the piezoelectric element was found to be in a linear relation with the moisture content measured by the paper moisture tester as shown in FIG. 4. The regression line therefor was represented by the equation:

$$y=-0.25x+5.75$$

where x represents the moisture content, and y represents the generated voltage.

The moisture content in the FB75 paper sheet of unknown moisture content can be determined by measuring the generated voltage and conducting calculation according to the preliminarily prepared regression line. For example, in the aforementioned moisture measurement procedure, the generated voltage of 4.5 V shows a moisture content of 5% according to FIG. 4. In the above measurement, the time after contact of force-applying member 2 with sheet material 3 to voltage generation by pressure sensor 6 is only several milliseconds, so that the measurement including the calculation of the moisture content by the regression line can be completed within 0.1 second. Thus, the moisture measurement can be completed in a short time by use of the moisture-measuring device of this embodiment.

In FIG. 4, the generated voltage and the moisture content are in a linear regression relation. In some cases, according to the kind of sheet material 3 or conditions of external force application, the relation is in a curved regression. In this case also, the moisture content can naturally be detected by the same process. In the above embodiment, the calibration table was prepared at 25° C., but may be prepared in any temperature depending on the use or purpose. Since the moisture content varies in accordance with the atmospheric pressure, the regression function may be prepared at different atmospheric pressure when the atmospheric variation may cause a problem.

In the above explanation, force-applying unit 1 employs a cam and a spring. Otherwise, force-applying member 2 may be allowed to fall freely by use of a cam, or a solenoid may be used for the dropping. The force applying means for the external force generation is not limited at all.

The movement of force-applying member 2 toward sheet material 3 may be a uniform movement, a uniformly accelerated movement, or a random movement. The force may be applied to the sample sheet by one motion or plural motions with confirmation of reproducibility. Otherwise, the forces in different strengths may be applied, and the moisture content may be determined from the respective relations between the voltage for the strength of forces and the moisture content.

Pressure sensor 6 is not limited to the aforementioned piezoelectric element, but may be the one utilizing the piezoelectric effect of a ferroelectric substance, a piezoelectric substance, a pyroelectric substance, or a semiconductor substance. Instead, the positional shift by an external force of a dielectric substance placed between electrodes may be detected by measuring electric capacity between the electrodes. Otherwise, a volume change of a gas or a liquid may be measured optically. A strain meter may be used. A velocity-measuring means for measuring a velocity of a moving body such as a Doppler velocity meter may be used for measuring the velocity change of force-applying member 2. The pressure sensor utilizing a piezoelectric effect of a piezoelectric element, a semiconductor, or the like is preferably employed for a smaller size of the device. The most suitable one is selected to meet the use and the object.

In the above explanation, the peak value of the voltage transmitted from the piezoelectric element is measured. However, the electric signal for the measurement is not limited to the voltage. Also useful are a peak area intensity, a gradient of a voltage peak by waveform analysis, and a voltage in a prescribed frequency region obtained by frequency analysis. This frequency region is not limited. An audible region can be employed.

Sample sheet 3 need not be flat, and may be creased or wrinkled. For measurement of such a non-flat sheet, a mechanism for smoothing sample sheet 3 or preventing wrinkle formation may be provided in the device shown in FIG. 2. In some cases, the measurement may be conducted with sample sheet 3 stretched horizontally in FIG. 2. During the sheet delivery, sample sheet 3 may swing or vibrate. To prevent this, a sheet-pressing mechanism may be provided to suppress variation of the level difference between sample sheet 3 and pressure sensor 6 caused by the swing or vibration of the sample sheet.

In FIG. 2, sample sheet 3 is shown to be flat. However, measurement table 4 need not be flat. Measurement table may be curved and sample sheet 3 may be curved correspondingly, provided that sample sheet 3 is in stable contact with measurement table 4.

The strength of the force applied to sample sheet 3 is controlled not to damage or break sample sheet 3. In a case where the force-applied portion of the sheet should not be deformed irreversibly, the force strength is adjusted to cause recoverable elastic deformation, or to cause non-trouble-causing slight deformation of sheet 3. The number of times of the force application is not specially limited. When a motor and a cam are employed, for example, the force may be applied plural times by the cam shape. The plural forces may be applied at the same strength or at different strengths. The force need not be applied perpendicularly to sheet 3, but may be applied in any direction, provided that the output from the sensor can be detected.

A second embodiment is explained below.

Figure 5:
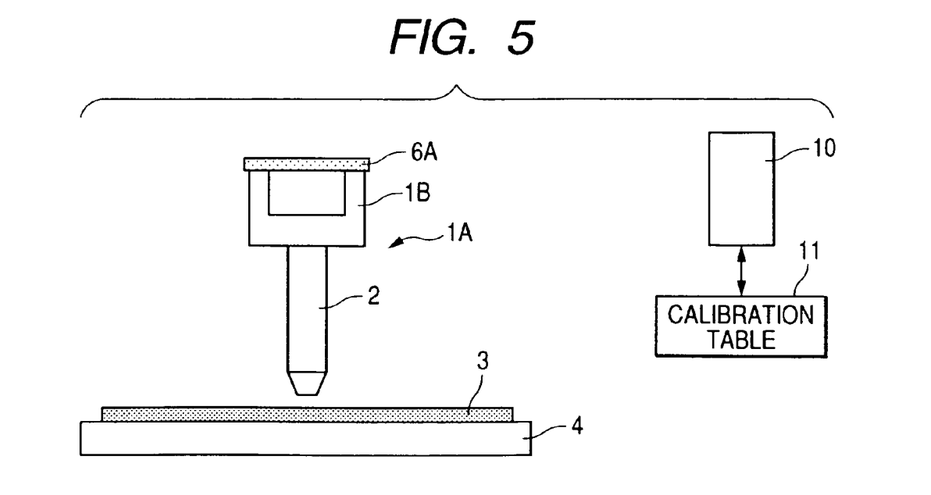
FIG. 5 illustrates schematically a constitution, of a device of an embodiment of the present invention.

FIG. 5 shows schematically the constitution of moisture-measuring device in this embodiment. In FIG. 5, the same symbols as in FIG. 2 are used for denoting the corresponding parts.

In FIG. 5, force-applying unit 1A has force-applying member 2, and pressure sensor 6A constituting an external force-detecting means, in integration. This force-applying unit 1A is allowed to fall freely by a motor and a cam not shown in the drawing. In this embodiment, main body 1B or the force-applying unit has been worked as shown in FIG. 5. Pressure sensor 6A as a piezoelectric element is fixed in a state of a beam on the upper face of main body 1B of the force-applying unit.

The strength of the external force to be applied is adjusted by the level difference between the tip of force-applying member 2 and the face of measurement table 4. Naturally, the strength of the external force may be adjusted by the distance between the tip of force-applying member 2 and the face of the sample sheet 3 since the external force depends on the thickness of sample sheet 3.

In this embodiment, force-applying member 2 is a round column of Derlin with the tip end rounded. Force-applying member 2 need not be made of a single material: for example, a metal part may be attached to the tip. The shape is not limited to a round column, but may be a prism, a sphere, or the like. Sample sheet 3 may be kept stopped or moving. Measurement table 4 may be made of any material including inorganic materials such as a metal, and a ceramic; organic materials such as an ABS resin; and composites of an organic material and an inorganic material. In measurement of a sample sheet moving for delivery as in a copying machine, the material of the measurement table is preferably selected which has a suitable frictional coefficient for the purpose, since the friction between the sample sheet and the table may cause a trouble in the sheet delivery or image formation.

The moisture of the sample sheet is measured through the steps below.

Firstly, sample sheet 3 is placed on measurement table 4. Force-applying unit 1A is allowed to fall from a predetermined height to apply an external force with force-applying member 2 to sample sheet 3. The weight of force-applying unit 1A which is constituted of force-applying member 2, main body 1B of the force-applying unit, and pressure sensor 6A has been adjusted to a prescribed weight. After force-applying unit 1A falls freely and collides against sample sheet 3, force-applying unit 1A allowed to rebound by rigidity of sample sheet 3, and to collide repeatedly against sample sheet 3.

In the repeated collision of force-applying unit 1A, the repulsion force (output) of sample sheet 3 acts on force-applying unit 1A to output plural signals from pressure sensor 6A. For example, with an inkjet recording paper sheet LC301 (Canon K.K.) as sample sheet 3, plural electric signals are outputted from pressure sensor 6A as shown in FIG. 6.

Figure 6:
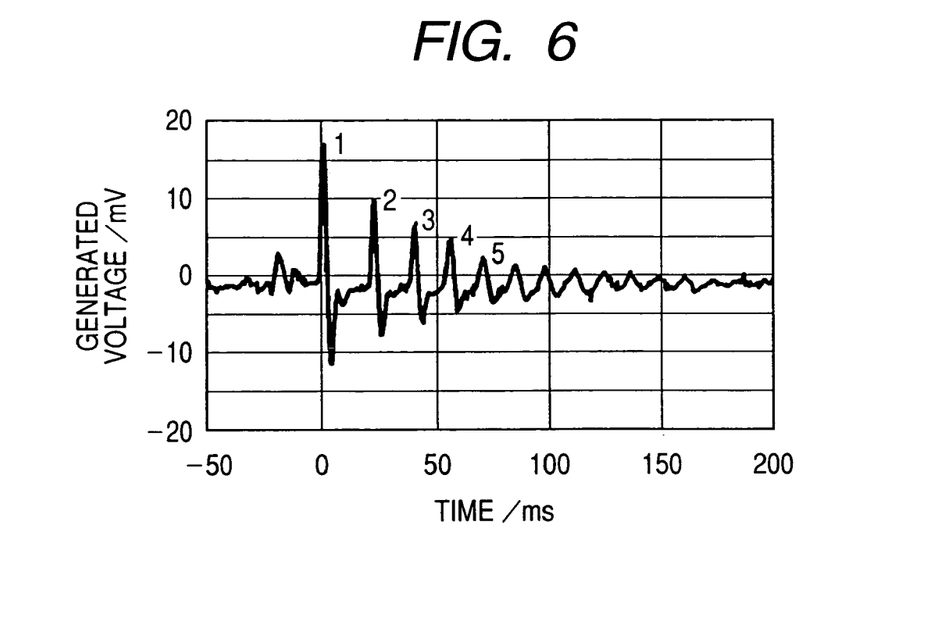
FIG. 6 shows an output from the sensor equipped in the above device.

In FIG. 6, force-applying unit 1A collides about ten times against sample sheet 3. In FIG. 6, the first to fifth voltage peaks are numbered. The moisture content may be measured, for example, from the generated voltage in comparison with the aforementioned calibration table. However, in this embodiment, with the observed first to n-th peaks, a calibration table is prepared regarding dependence of the time from the first collision to the (n-m)th collision (n-m≧2) on the moisture content, and the moisture content in sample sheet 3 is detected by comparison of the time interval between the peaks with the calibration table.

In FIG. 6, for example, the fifth collision occurs 71 milliseconds after the first collision. The moisture content is measured from the time for the repeated collision.

Figure 7:
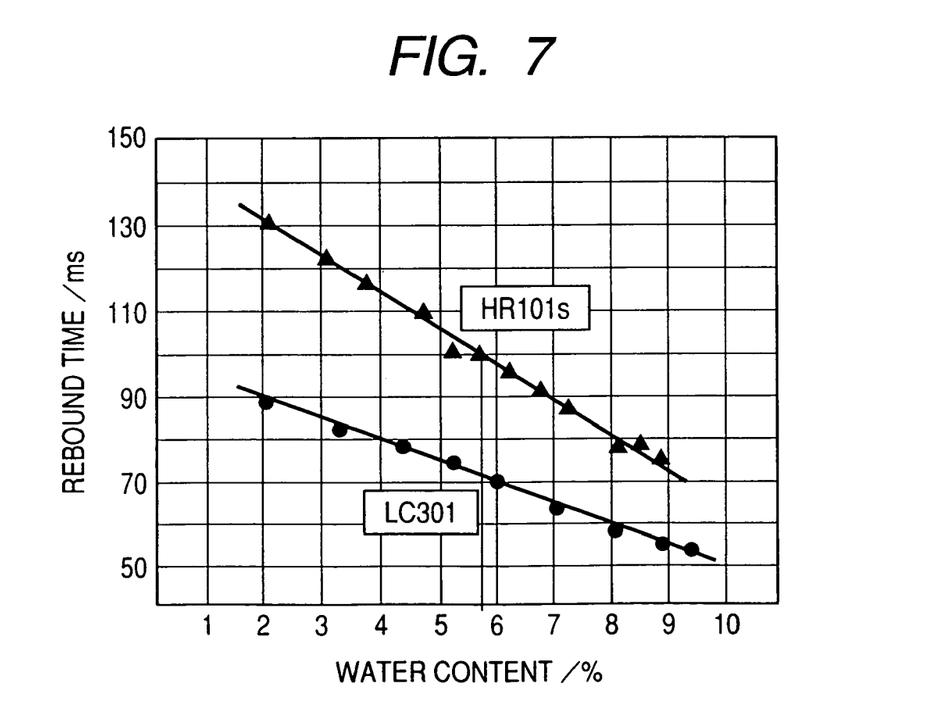
FIG. 7 shows results of measurement with the above device.

FIG. 7 shows, as an example, the calibration tables for inkjet recording paper sheets LC301 and HR101s (both from Canon K.K.). The calibration tables are prepared, for the fall of force-applying unit 1A of 8 g in weight from a height of 3 mm above the surface of measurement table 4, by plotting the time from the first rebound to the fifth rebound as the ordinate and the moisture contents measured by a paper moisture tester as the abscissa. The measurement is conducted at 25° C. The moisture contents of the paper sheets are measured (detected) after the paper sheets are conditioned for 48 hours in a closed humidity-controlled container.

FIG. 7 is useful as the calibration table measurement of the moisture content of an unknown sample. For example, for the paper sheet HR101s, the relation between the rebound time y (milliseconds) in the ordinate and the moisture content x (%) in the abscissa in FIG. 7 is represented by a regression line:

$$y=-8.1x+146.2$$

From this regression line, the rebound time of 100 milliseconds corresponds to moisture content of 5.7%.

Not only by the rebound time, the moisture content can be measured by the voltage peak shape, the voltage peak breadth, the voltage peak gradient, the voltage peak area, detection of specific frequency band by frequency analysis, or the like or combination thereof.

As described above, the moisture contained in a sample sheet can be measured in a shorter time with a smaller-sized device by applying a predetermined dynamic force onto sample sheet 3 and measuring the output from sample sheet 3 in response to the applied external force.

In the above explanation, the moisture measurement is conducted based on the rigidity change of sample sheet 3 depending on the moisture content. The present invention is not limited thereto. The moisture content can be measured based on other dynamic properties of sheet 3 varying as a function of the moisture content, such as the Young modulus, the density, and sheet thickness.

Further, in the above explanation, an electric signal from a pressure sensor (piezoelectric element) is utilized in the moisture measurement. The present invention is not limited thereto. An optical or magnetic output corresponding to the absorption, propagation, amplification, or repulsion of the external force by sample sheet 3 may be utilized for the moisture measurement (or detection).

The present invention is explained more specifically by reference to Examples. Incidentally, in Examples below, a piezoelectric element is used as the pressure sensor, but is not limited thereto. The materials for the constitution parts are not limited also.

EXAMPLE 1

Moisture was measured with a moisture-measuring device shown in FIG. 2.

In this Example, force-applying member 2 was a stainless-steel round column of 3.5 mm diameter, having a weight of 4 g adjusted by controlling the length, and having a flat tip end. Measurement table 4 for placing sample sheet 3 was a stainless steel plate of 2 mm thick, having rectangular aperture 41 of 10 mm×30 mm at the center. Force-receiving member 5 was a stainless steel plate of 5 mm×5 mm and 1.5 mm thick. Piezoelectric element 6 had a size of 5 mm×10 mm and 30 μm thick. Damping member 7 was a nitrile rubber of 5 mm×5 mm and 2 mm thick. The force-receiving member 5, piezoelectric element 6, and damping member 7 were bonded by an adhesive together and were placed so as to have a center line common to aperture 41 formed in measurement table 4.

Pedestal 8 for fixing force-receiving member 5, piezoelectric element 6, and damping member 7 was a stainless steel plate of 7 mm×60 mm and 5 mm thick, and was fixed by screws not shown in the drawing. The level difference between the face of measurement table 4 and force-receiving member 5 was adjusted to 0.2 mm. The electric signals from piezoelectric element 6 may be taken, for example, by an oscilloscope or a general-purpose voltage detection circuit (not shown in FIG. 2). In this Example, the electric signals were introduced through a personal computer into an oscilloscope, and the moisture content was calculated by a personal computer (moisture detecting means).

Printer paper sheets FB75 (Fox River Bond Co.) were used as the measurement sample. The paper sheets were kept for 48 hours in an environmental test chamber of constant humidity at 25° C. Thereafter the moisture contents of the paper sheets after 48-hour conditioning were measured by a paper moisture tester in the environmental test chamber. The paper sheets after the moisture measurement were set on the moisture-measuring device shown in FIG. 2.

Then instruction was outputted from a personal computer (not shown in the drawing) to force-applying unit 1 to apply an external force to paper sheet 3. The signals from piezoelectric element 6 were detected by an oscilloscope, and the maximum voltage generated was introduced through the memory of the oscilloscope to the personal computer.

The measurement was conducted 20 times respectively with paper sheets of various moisture contents by the above moisture-measuring device and the paper moisture tester. The correlation of the average of the voltage with the average moisture content is shown in the aforementioned FIG. 4. The moisture content x and the generated voltage y were in a linear relation as shown in FIG. 4, the regression function being represented by the following equation:

$$y = -0.25x + 5.75$$

This regression line was stored in the memory of the personal computer as the calibration table.

After preparation of the calibration table, a paper sheet FB75 of an unknown moisture content was placed on measurement table 4. An external force was applied to the paper sheet (Steps 1 and 2). In this Example, the external force was applied ten times repeatedly. The voltages generated in pressure sensor 6 were found to be 0 volt four times and 4.1 volts six times.

From comparison of the above results with the memorized regression line as the calibration table, the moisture content was found to be 6.76%. The measurement error was ±0.2% estimated from the variation of the detected voltage. The time for one measurement was about 20 milliseconds after giving a signal of rotation to the motor. Since the rotation rate of the motor was 50 milliseconds per rotation, the time for the ten repetition of measurement was 0.5 second.

Paper sheets, FB75, having been conditioned at 25° C. and 85% RH for 35 hours, and other paper sheets, FB75, having been conditioned at 25° C. and 15% RH for 24 hours were transferred to an environment of 25° C. 52% RH. Ten minutes after the transfer, the moisture contents were measured. The paper sheet conditioned at 25° C. and 85% RH gave detected voltages of 3.6 volts immediately after the transfer and 3.8 volts 3 minutes after the transfer. This showed that the moisture content of the paper sheet became changed from 8.6% to 7.8%.

The paper sheet conditioned at 25° C. and 15% RH gave detected voltages of 5.1 volts immediately after the transfer and 4.7 volts 5 minutes after the transfer. This showed that the moisture content of the paper sheet changed from 2.6% to 4.2%. The moisture content values measured by an optical paper moisture tester for the same environmental change as above agreed with the above measurement results within an error of about 0.1%. The time for one measurement by the optical paper moisture tester is about 2 to 3 seconds, thus ten measurements requiring 20 seconds or more in total. Therefore, the moisture-measuring device of this Example can shorten the moisture measurement time.

Incidentally the materials of the sheets of the object of the present invention are usually composed mainly of cellulose. In measurement of the moisture of a cellulosic material by an optical means like a spectroscope, the cellulose causes two types of light absorption: absorption by oxygen-hydrogen bonding in the cellulose, and absorption by oxygen-hydrogen bonding of the moisture contained in the sheet material. Therefore, in the measurement of the light absorbance, the above two types of absorption should be discriminated. Accordingly, optical measurement of the moisture requires measurement time of several seconds generally.

EXAMPLE 2

Figure 8:
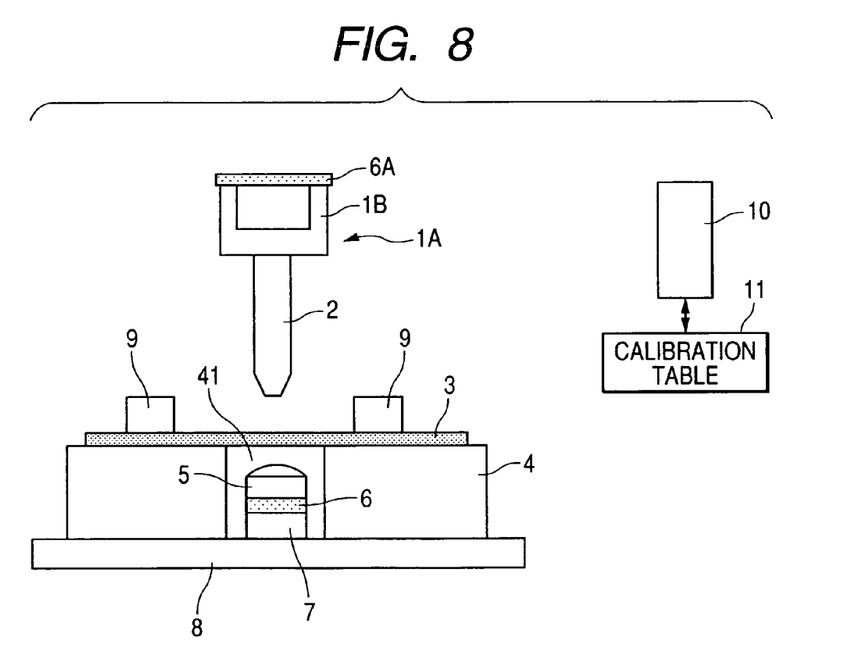
FIG. 8 illustrates schematically a constitution of a device of an embodiment of the present invention.

Moisture was measured with a moisture-measuring device shown in FIG. 8.

The moisture-measuring device shown in FIG. 8 employed force-applying member 1A shown in FIG. 5 in place of force-applying member 1 shown in FIG. 2. With force-applying member 1A shown in FIG. 5, the external force applied to sample sheet 3 could be detected by piezoelectric element (pressure sensor) 6A provided with force-applying member 2 on force-applying unit 1A on the upper side of sample sheet 3 as well as by piezoelectric element (pressure sensor) 6 placed at the bottom of force-receiving member 5.

In this Example, the moisture content can be measured by either one of piezoelectric elements 6 and 6A or the both thereof. However, with the upper piezoelectric element 6A, the moisture content is preferably measured by the rebound time rather than the generated voltage. With the lower piezoelectric element 6, the moisture content may be measured by any of the rebound time and the first voltage peak.

If the moisture contents measured by the two piezoelectric elements 6 and 6A are different significantly from each other, the measurement is considered to be erroneous. Thus the preciseness of the measurement can be judged by comparison of the two measurement results.

In this Example, the upper piezoelectric element 6A had a size of 1.5 mm×25 mm and 0.4 mm thick. Force-applying unit 1A was 8 g in weight and made of brass. Force-applying member 2 was a stainless-steel round column of 4 mm diameter, having conical top portion with a flat tip end of 1 $mm^2$ in area.

In FIG. 8, the numeral 9 indicates a brass block having a size of 10 mm×10 mm×30 mm. In this Example, two blocks 9 were employed as a pressing mechanism for pressing sample sheet 3. After setting sample sheet 3, blocks 9 were placed manually at positions nearly symmetrically to aperture 41.

Measurement table 4 for placing sample sheet 3 had an ellipsoidal aperture 41 having a major axis of 30 mm and a minor axis of 15 mm. Force-receiving member 5 having a top face convexing upward, piezoelectric element 6, and damping rubber 7 were fixed on pedestal 8 to have a center line common to aperture 41.

The level difference between the face of measurement table 4 and the top of force-receiving member 5 was 0.3 mm. Force-receiving member 5 had a size of 7 mm×10 mm. FIG. 8 shows a view taken from the 7-mm side of the force-receiving member. The force-receiving member 5 had a convex end face of a curvature of 90 mm diameter, and the maximum thickness of 2.5 mm. Piezoelectric element 6 had a size of 7 mm×10 mm and 0.3 mm thick. Damping rubber 7 was made of silicon rubber of 7 mm×9 mm and 2 mm thick.

Force-applying unit 1A was allowed to fall freely from a height of 4 mm above measurement table 4. FIG. 6 mentioned before shows the output from piezoelectric element 6A. In this measurement, the temperature was 25° C. and the humidity was 58% RH. Sample sheet 3 was an inkjet recording paper sheet LC301 (Canon K.K.). Force-applying unit 1A rebounded from the sample sheet and collided against it repeatedly. Correspondingly, piezoelectric element 6A outputted plural voltage peaks as shown in FIG. 6.

In this Example, the time from the first voltage peak to a prescribed order number of the peak was measured since a low rigidity of piezoelectric element 6A may cause deformation during falling. In this Example, the time from the first peak to the fifth peak was measured. The fifth voltage peak was observed 71 milliseconds after the first voltage peak.

On application of an external force to sample sheet 3 by force-applying unit 1A (or force applying member 2), a voltage was generated by piezoelectric element 6 as well as by piezoelectric element 6A. In this measurement, the output voltage is basically similar to that shown in FIG. 6. With a sheet of LC301, the voltage generated by piezoelectric element 6 was observed to be about half that of piezoelectric element 6A, and only three peaks were clearly observed.

On the other hand, the calibration table showing the relations of the moisture content and the signal voltage were derived for the inkjet recording paper sheets C301 and HR101s as below.

The objective sample sheets, the moisture-measuring device of the present invention, and a commercial paper moisture tester were kept at 23° C. for 48 hours in an environmental test room in which the humidity is controllable.

Thereafter, the sample sheets were subjected to measurement with the moisture-measuring device to detect the generated voltage of at least one of piezoelectric elements 6 and 6A. In the measurement with piezoelectric element 6A, the time from the first rebound to the fifth rebound was measured. Separately the moisture content was measured by the paper moisture tester. This test was repeated by changing the humidity of the environmental test room to obtain the correlation of the rebound time with the moisture content as shown in FIG. 7.

In the above measurements, the two kinds of the sample sheets gave respectively a linear regression relation. The rebound time y (milliseconds) was a function of the moisture content x (%) as shown by the linear regression equation:

$$y=-4.7x+99 \text{ for } LC301$$

$$y=-8.1x+148.9 \text{ for } HR101s$$

In measurement with piezoelectric element 6, the first peak voltage y (millivolts) was a function of the moisture content x (%) as shown by the linear regression equations:

$$y=-4.6x+7.9 \text{ for } LC301$$

$$y=-8.1x+21 \text{ for } HR101s$$

The above relations were utilized as the calibration table.

Paper sheets, LC301 and HR101s, having been conditioned in various environments were subjected to measurement with the moisture-measuring device of the present invention and with the paper moisture tester, and the measurement results were compared.

Consequently, the results according to the two measurement methods agreed within error of ±0.1% for the sample sheets conditioned in 20 different environmental conditions (temperature: 20–28° C., humidity: 10–85% RH) for 48 hours. For example, the sample sheets of LC301 and HR101s kept at 23° C. and 85% RH were found to contain moisture of 8.5% and 8.7% respectively by the moisture-measuring device of the present invention, and 8.5% and 8.8% respectively by the paper moisture tester.

In the above measurement, the external force was applied by one free falling of the force-applying member. The required measurement time was 0.15 second or less for HR101s with piezoelectric element 6, whereas with the paper moisture tester, one measurement took a time of 2 to 3 seconds.

The measurement errors with the piezoelectric elements 6 and 6A were not larger than 0.1% for the sheets LC301, and HR101s. Incidentally, for comparison, an LC301 sheet was crumpled by hands to cause wrinkles and was subjected as it was to the measurement. As the results, the measured values by piezoelectric elements 6 and 6A were different by 10% or more, showing the measurement result not to be reliable.

EXAMPLE 3

The moisture-measuring device shown in FIG. 2 is mounted on an image-forming apparatus such as a copying machine, an LBP, and an inkjet printer.

Figure 9:
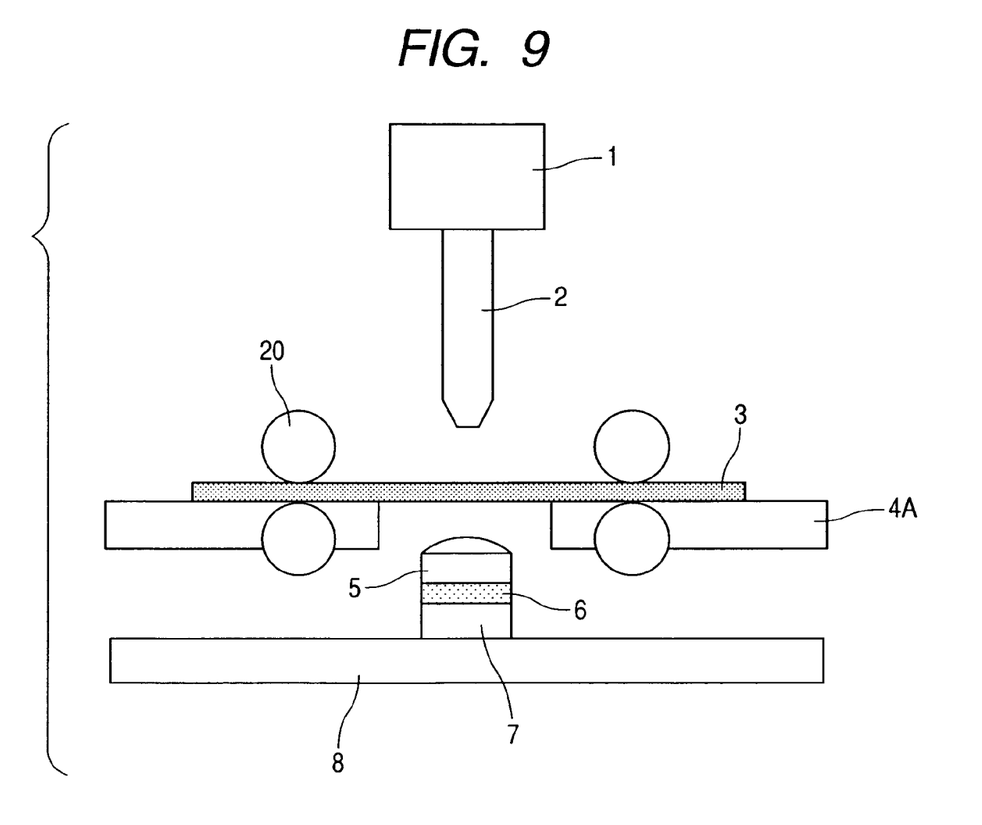
FIG. 9 illustrates an example of an image-forming apparatus equipped with the device of the present invention.

FIG. 9 illustrates constitution of a portion of an image-forming apparatus having a moisture-measuring device of the present invention and an image-forming assembly not shown in the drawing for forming an image on sheet 3. In FIG. 9, the symbol 4A denotes a sheet delivery table of a sheet delivery system of the image-forming apparatus. Sheet 3 is delivered at a prescribed speed along the upper face of this sheet delivery table 4A. Sheet delivery table 4A has aperture 41,. The shape of the aperture is not limited, and may be circular, ellipsoidal, or corner-rounded pentagonal, provided that the aperture does not interfere with the delivery of sheet 3.

The numeral 20 denotes rollers for delivering sheet 3. Rollers 20 are not limited at all in the set position, the shape, and the material. In FIG. 9, two pairs of rollers 20 are employed for delivery of the sheet, but are not limited thereto. The external force may be applied to the sheet delivered by either one pair of rollers. Incidentally a mechanism for preventing flutter of the sheet may be provided between the pairs of rollers.

In this Example, the start of delivery of sheet 3 from a sheet tray (not shown in the drawing) of the image-forming apparatus is confirmed by a sensor (not shown in the drawing). After a prescribed time from the confirmation of the start of the sheet delivery, force-applying unit 1 drives a motor to move force-applying member 2 by a cam and a coil spring to apply a force to sheet 3. In this Example, the cam is designed to apply the force twice in one rotation of the motor, first strongly and second weakly.

Force-applying member 2 is a stainless-steel round column having a conical tip portion with a flat tip end face of 1 mm$^2$ in area as shown in FIG. 9, and having a weight of 4.8 g. The coil and the cam not shown in the drawing were designed so that force-applying member 2 impacts sheet 3 at a rate of 0.48 m/s, and 0.24 m/s. Force-receiving member 5 is made of stainless steel having a convex top face, having a maximum thickness of 4 mm and a size of 5 mm×7 mm. The level difference between the apex of the convex of force-receiving member 5 and the lower face of sheet 3, or the face of sheet delivery table 4, is 0.2 mm. Piezoelectric element 6 has a size of 5 mm×7 mm and 50 µm thick. Damping member 7 is made of silicone rubber, having a size of 5 mm×7 mm and 2 mm thick.

With the above constitution, A4-sized recording paper sheets FB75 (Fox River Bond Co.) were delivered at a delivery rate of 50 sheets per minute. Force-applying member 2 was brought into contact with the FB paper sheets twice. The output from piezoelectric element 6 was detected by a voltage-detecting circuit (not shown in the drawing). Thereby two voltage peaks were observed as shown in FIG. 10.

Figure 10:
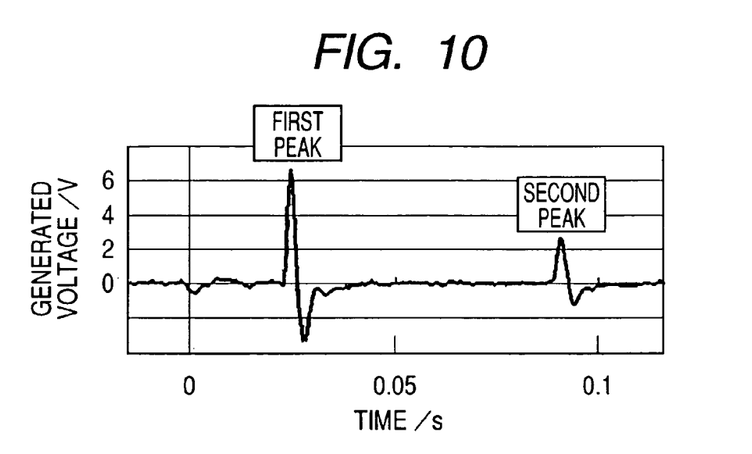
FIG. 10 shows an output from the sensor equipped in the above device.
Figure 11:
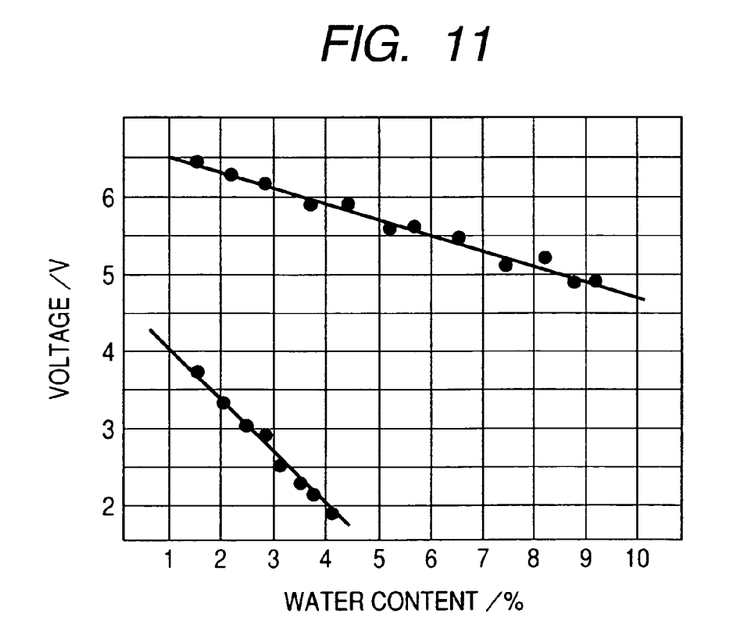
FIG. 11 shows results of measurement with the above device.

In FIG. 10, the first peak corresponds to the voltage generated on contact of force-applying member 2 with the FB 75 sheet at a rate of 0.48 m/s, and the second peak corresponds to the generated voltage on contact at a rate of 0.24 m/s. FIG. 11 shows the correlation of the peak voltage with the moisture content.

The voltage y (V) and the moisture x (%) were in the relation of the regression function below:

$y=-0.22x+6.83$ at the first time $y=-0.63x+4.63$ at the second time

In the second force application in which the applied force is weak, the voltage is not generated in a higher moisture content range. However, as understood from FIG. 11, the steep gradient of the regression line of the second force application enables observation of slight moisture content variation in comparison with the first force application.

In the above measurement, the paper sheets were kept at a temperature of 23° C. for 48 hours in a humidity-controlled environmental test room before the measurement. Even when the moisture-measuring device was brought into the environmental test room immediately before the measurement, the measurement results were not affected significantly by the temperature difference of not more than 15° C. Incidentally the linear regression relation was memorized preliminarily in the memory (not shown in the drawing) in the image-forming apparatus.

The moisture-measuring device of this Example was installed in front of registration rollers of an image-forming apparatus. A bundle of 300 paper sheets was stored in a sheet tray. With this apparatus, the same printing was conducted repeatedly at a printing rate of 50 sheets of FB75 paper per minutes in six lots of 50 sheets at lot intervals of 5 minutes. Before and during the printing, the apparatus was kept at 23±2° C. and 10–13% RH. The moisture content of the recording paper sheets was 4.1% immediately after taking out from a package bag as measured by a paper moisture tester.

In the printing experiment, firstly, printing was conducted without operation of the moisture-measuring device under constant printing conditions (toner transfer voltage: 8 kV, fixation temperature: 190° C.) in lots of 50 paper sheets at lot intervals of 5 minutes. During the printing, the ratio of toner transfer onto the paper sheets became lower at the third and subsequent lots to cause printing failure. At the time of the printing of the third lot, the moisture content of the FB75 paper sheet was 3.2% as measured by the paper moisture tester. Thus the moisture content was found to have decreased after unsealing of the paper package bag.

Next, before starting the toner transfer onto the printing paper sheet, the moisture content of the printing paper sheet was measured by the moisture-measuring device, and the toner transfer voltage was adjusted to meet the measured moisture. Prior to this measurement, the correlation between the paper moisture and the optimum transfer voltage had been derived preliminarily and had been memorized in the memory unit of the image-forming apparatus.

Thereafter, a bundle of 300 sheets of FB75 paper was taken out from a package and was placed in a recording paper sheet tray. The printing was conducted in lots of 50 sheets at lot intervals of 5 minutes. The environment of the image-forming apparatus was the same as above. Of the printing conditions, only the toner transfer voltage was adjusted to meet the measured moisture. Thus, the printing could be conducted with all of the 300 sheets without printing failure.

The change of the moisture content was monitored with the paper moisture tester. The moisture changed from 4.2% at the first printing lot, to 3.1% at the third lot, and 2.8% at the sixth lot. The toner transfer voltage was changed in correspondence with the change of the moisture content: 1.8 kV for the first lot, 2.5 kV for the third lot, and 2.8 kV for the sixth lot. Thereby the transfer failure could be prevented, whereby printing failure could be prevented.

In the above-described printing, since the moisture content was in a lower region, the regression line for the second force-application was used. When the moisture content is higher to lower the generated voltage on the second force-application or to make the voltage unobservable, the regression line for the first force-application is useful naturally.

In the image-forming apparatus of the present invention, the printing is conducted at 0.2 second after passage of the recording paper sheet through the registration rollers, whereas the moisture can be measured within 0.1 second as shown in FIG. 10. Therefore the moisture can be measured without stopping the sheet delivery and without decreasing the printing speed.

This application claims priority from Japanese Patent Application No. 2004-169114 filed Jun. 7, 2004, and Japanese Patent Application No. 2005-146036 filed May 18, 2005 which are hereby incorporated by reference herein.

What is claimed is:

1. A moisture content-acquiring device for acquiring data on moisture contained in a sheet, comprising:
    a force-applying unit for applying an external force to the sheet;
    a force-receiving unit for receiving the external force through the sheet;
    a signal outputting unit for outputting a signal reflecting a mechanical property of the sheet, which signal outputting unit is placed on at least one of the force-applying unit and the force-receiving unit, and which output signal is acquired through application of the external force; and
    a moisture content-acquiring unit for acquiring data on moisture of the sheet based on the signal from the signal outputting unit, which moisture content-acquiring unit acquires the moisture content of the sheet by a comparison of the signal acquired through application of the external force from the signal outputting unit with data stored in a memory, the data on a relation between a moisture content in the sheet and the signal from the signal outputting unit.

2. The moisture data-acquiring device according to claim 1, wherein the force-applying unit applies the external force plural times to the sheet.

3. The moisture data-acquiring device according to claim 1, wherein a position-defining means is provided for defining the position of the sheet to keep a constant distance between the force-receiving unit and the sheet.

4. The moisture data-acquiring device according to claim 1, wherein the force-applying unit applies an external force to the sheet to bend and bring the sheet into contact with the force-receiving unit, and the contact causes output of the signal from the signal outputting unit.

5. The moisture data-acquiring device according to claim 1, wherein the sheet is bent from the position of the sheet before the contact with the force-receiving unit by a concave or a groove provided on a side of the sheet on which the force-receiving unit is located.

6. An image-forming apparatus, comprising the moisture data-acquiring device set forth in claim 1 and an image forming assembly for forming an image on a sheet, wherein a condition for image formation is adjusted based on the data from the moisture content-acquiring device.

7. An image-forming apparatus, comprising the moisture data-acquiring device set forth in claim 1, an image forming assembly for forming an image on a sheet and a delivery means for delivering the sheet, wherein a condition for delivering sheet are adjusted based on data from the moisture content-acquiring device.

* * * * *

UNITED STATES PATENT AND TRADEMARK OFFICE
CERTIFICATE OF CORRECTION

PATENT NO. : 7,212,929 B2  Page 1 of 1
APPLICATION NO. : 11/144647
DATED : May 1, 2007
INVENTOR(S) : Norio Kaneko et al.

It is certified that error appears in the above-identified patent and that said Letters Patent is hereby corrected as shown below:

COLUMN 1:
Line 38, "wanted." should read --needed.--.

COLUMN 3:
Line 29, "several, times" should read --several times--.
Line 60, "controls" should read --control--.

COLUMN 14:
Line 28, "A-bundle" should read --A bundle--.

COLUMN 16:
Line 35, "sheet" should read --the sheet--.

Signed and Sealed this

Eighteenth Day of December, 2007

JON W. DUDAS
*Director of the United States Patent and Trademark Office*